United States Patent
Duewer (10) Patent No.: US 10,772,594 B2
(45) Date of Patent: Sep. 15, 2020

(54) METHODS, SYSTEMS, APPARATUSES, AND COMPUTER PROGRAM PRODUCTS FOR EXTENDING THE FIELD OF VIEW OF A SENSOR AND OBTAINING A SYNTHETIC RADIAGRAPH

(71) Applicant: DENTSPLY SIRONA Inc., York, PA (US)

(72) Inventor: Frederick William Duewer, Woodside, NY (US)

(73) Assignee: DENTSPLY SIRONA Inc., York, PA (US)

(*) Notice: Subject to any disclaimer, the term of this patent is extended or adjusted under 35 U.S.C. 154(b) by 92 days.

(21) Appl. No.: 16/215,738

(22) Filed: Dec. 11, 2018

(65) Prior Publication Data

US 2019/0175131 A1   Jun. 13, 2019

Related U.S. Application Data (60) Provisional application No. 62/640,267, filed on Mar. 8, 2018, provisional application No. 62/597,189, filed on Dec. 11, 2017.

(51) Int. Cl.
*A61B 6/00* (2006.01)
*G06T 11/00* (2006.01)
*A61B 6/14* (2006.01)
*A61B 6/02* (2006.01)

(52) U.S. Cl.
CPC ............ *A61B 6/5205* (2013.01); *A61B 6/025* (2013.01); *A61B 6/14* (2013.01); *G06T 11/006* (2013.01); *G06T 11/008* (2013.01); *G06T 2211/424* (2013.01); *G06T 2211/436* (2013.01)

(58) Field of Classification Search
CPC ......... A61B 6/5205; A61B 6/025; A61B 6/14; G06T 11/006; G06T 11/008
See application file for complete search history.

(56) References Cited

U.S. PATENT DOCUMENTS

| | | | |
|---|---|---|---|
| 10,643,354 B2* | 5/2020 | Wang | A61B 6/5205 |
| 2011/0142314 A1* | 6/2011 | Hsieh | A61B 6/032 382/131 |
| 2013/0028500 A1* | 1/2013 | Takahashi | A61B 6/032 382/132 |
| 2014/0193055 A1* | 7/2014 | Takahashi | G06T 11/006 382/131 |
| 2014/0233847 A1* | 8/2014 | Ratcliff | G06K 9/00228 382/154 |

(Continued)

Primary Examiner — Utpal D Shah
(74) Attorney, Agent, or Firm — Dentsply Sirona Inc.

(57) ABSTRACT

A method, apparatus, system, and computer program product for using an invalidity matrix, iterative reconstruction and reprojection to generate a two-dimensional image. The method includes acquiring projections through an a dental anatomy, calibrating the acquired projected images, estimating a geometry of the tomosynthesis system, determining an invalidity matrix for each acquired projection image, removing contributions of marker particles to the acquired projection images, constructing a starting volume for reconstruction, performing an iteration process for iteratively updating the starting volume, and reprojecting a final reconstructed volume to obtain a final two-dimensional image.

21 Claims, 8 Drawing Sheets

(56) References Cited

U.S. PATENT DOCUMENTS

| | | | |
|---|---|---|---|
| 2014/0247264 A1* | 9/2014 | Sundberg | G06T 11/006 345/424 |
| 2015/0185859 A1* | 7/2015 | Yamamoto | G06F 3/017 345/156 |
| 2016/0005192 A1* | 1/2016 | Royalty | G06T 11/003 382/131 |
| 2016/0220212 A1* | 8/2016 | Duewer | A61B 6/5252 |
| 2017/0004636 A1* | 1/2017 | Nett | A61B 6/5264 |
| 2017/0186195 A1* | 6/2017 | Lin | A61B 6/5282 |
| 2018/0018757 A1* | 1/2018 | Suzuki | A61B 6/03 |
| 2018/0018768 A1* | 1/2018 | Hsu | A61B 6/5217 |
| 2018/0268570 A1* | 9/2018 | Budagavi | G06T 9/001 |
| 2019/0142357 A1* | 5/2019 | Fan | A61B 6/4035 600/425 |

\* cited by examiner

Maxillary Posterior: Size 1

FIG. 10

Maxillary Posterior Extended Field : Size 1 (vertical)

FIG. 11

METHODS, SYSTEMS, APPARATUSES, AND COMPUTER PROGRAM PRODUCTS FOR EXTENDING THE FIELD OF VIEW OF A SENSOR AND OBTAINING A SYNTHETIC RADIAGRAPH

CROSS REFERENCE TO RELATED APPLICATIONS

This application claims benefit of provisional applications 62/597,189, filed on Dec. 11, 2017 and 62/640,267, filed on Mar. 8, 2018 which are incorporated herein by reference in their entirety.

FIELD

The present application relates generally to obtaining intraoral images in a dental environment, and, more particularly, to a method, system, apparatus, and computer program product for using an invalidity matrix, iterative reconstruction and reprojection to generate from a three-dimensional (3D) reconstructed volume a two-dimensional (2D) image with image artifacts removed wherein the 3D reconstructed volume is based on a plurality of projection images. Herein, the field-of-view of an x-ray sensor/detector is extended to generate a two-dimensional (2D) image that has a greater area than the area of the sensor/detector. The two-dimensional image is generated based on images taken at different x-ray source positions, along with an iterative reconstruction algorithm in combination with a reprojection algorithm that minimizes geometric distortion while maximizing field-of-view. Also discussed is the generation of a synthetic radiograph with noise comparable to a standard (non-synthetic) radiograph to allow for a two-dimensional radiograph that does not include marker particles.

BACKGROUND

X-ray radiography can be performed by positioning an x-ray source on one side of an object (e.g., a patient or a portion thereof) and causing the x-ray source to emit x-rays through the object and toward an x-ray detector located on the other side of the object. As the x-rays pass through the object from the x-ray source, their energies are absorbed to varying degrees depending on the composition of the object, and x-rays arriving at the x-ray detector form a two-dimensional x-ray image (also known as a radiograph) based on the cumulative absorption through the object.

Intraoral radiography is a technique in which an imaging sensor is placed inside the mouth of a patient and an x-ray source outside the mouth is used to irradiate the sensor with x-rays. The x-ray attenuation of hard tissues in the mouth results in a clinical image being formed on the sensor. Intraoral x-ray images provide a high level of detail of the tooth, bone, and supporting tissues. They also allow dentists to find cavities, examine tooth roots, evaluate the condition of the bony area around the tooth, determine if periodontal disease is present or a concern, and monitor the status of developing teeth, among other things.

First, increasing the applied x-ray dose typically improves the number of x-ray photons contributing to the image. Given that x-ray images are typically dominated by Poisson noise, the signal-to-noise ratio (SNR) improves as additional x-ray dose is applied. A minimum x-ray dose is therefore typically required to successfully visualize a given feature of clinical interest. Beyond that dosage, increasing dosage does not necessarily result in significant additional clinical utility.

Conventional x-ray imaging, discussed above, produces a two-dimensional image. Tomosynthesis however provides three-dimensional information about a patient in the form of tomographic image slices reconstructed from x-ray images of the patient taken from multiple perspectives within a scan angle smaller than that of computed tomography (CT) or cone-beam computed tomography (CBCT) (e.g., ±20°, compared with at least 180° in CBCT). However, tomosynthesis is a relatively undeveloped field in dentistry.

In both traditional x-ray imaging and tomosynthesis, an intraoral sensor/detector may be placed in a patient's mouth. For diagnostic images that include multiple teeth or for diagnostic tasks requiring entirely capturing a single tooth in an image, the size of a typical intraoral sensor can be prohibitive. A human's intraoral cavity has limited space, and thus the physical size of the intraoral sensor is also limited. In addition, patients may have certain conditions (e.g., dental tori) that restrict the use of intraoral sensors due to patient discomfort. There have been several approaches to increasing the field-of-view of the intraoral sensor. Some approaches focus on physical changes to the intraoral sensor. For example, one approach has been to use intraoral sensors with cut-off corners thereby making them easier to fit into the mouth. While this may allow for a larger intraoral sensor, this approach only marginally increases the field of view. Another approach has been to develop flexible intraoral sensors. This approach, however, requires significant changes in manufacturing parameters and does not appreciably increase the field of view. Another approach has been to capture and combine a series of images taken with parallel illumination. However, the typical system geometries for intraoral imaging result in significant stitching artifacts with this approach, causing misalignment between subvolumes to be combined. Other approaches rely on reconstruction methods to increase the reconstructed volume. These approaches are for external (i.e., non-intraoral) tomographic imaging systems where sample to be imaged is rotated, something which is impossible to achieve intraorally.

Therefore, it would be desirable to have a device, method and computer program products that could increase the effective size of a sensor to allow for viewing more teeth than can be seen with a standard sensor or, conversely, obtaining a standard size intraoral image on a patient who is unable to tolerate a sensor of standard size.

Further, intraoral x-ray imaging is a known and commonly used technology that is used to screen for caries and other dental pathologies. Instead of acquiring a single image using a stationary x-ray source, a series of images are taken while varying the source position in a known way. That series of images may be used to construct an estimate of the x-ray attenuation coefficient in the sampled volume. Intraoral radiography is a known and familiar technology which clinicians have considerable experience in evaluating. Therefore, providing both an intraoral radiograph and a dental tomosynthesis scan to a clinician will improve diagnostic capability. This has been solved in the past by presenting a center projection of a tomosynthesis scan as a radiograph. However, the center projection is not equivalent to a high dose radiograph because each projection of a tomosynthesis scan is typically taken at low dose. Another solution has been attempted in the past by moving the scanned x-ray source to the center of the scan position and then acquiring a high dose intraoral radiograph. However, this solution also increases the delivered dose to the patient by necessitating an additional high dose image which is not desirable.

In the case of breast tomosynthesis, a solution to generating a single two-dimensional image with significantly higher signal-to-noise ratio has involved reconstructing the tomosynthesis scan and then reprojecting the resulting volume to obtain a low noise mammogram by summing slices of the volume. Herein, non-iterative reconstruction methods are used wherein projections are acquired and filtered using a generalized Fourier filter. The filtered projection images are then backprojected to create a reconstructed volume. The reconstructed volume may then be reprojected to obtain a 2D image by summing slices that make up reconstructed volume. Filtered backprojection is a common non-iterative reconstruction technique. Each image is filtered and backprojected through a volume. The filter is typically chosen so that backprojections through the volume match the original projections. Artifacts may be minimized by smoothly extrapolating the input images so that the extrapolated images cover the full extent of the reconstructed volume. Unfortunately, this solution generates image artifacts when high contrast features move off of the field of view because the projection extensions are attempting to extrapolate large, high-frequency features, which is difficult to achieve.

Another problem with this solution is that the images taken during the scan contain information from different, overlapping volumes. The contrast variations are however relatively small. This method has therefore not been previously applied to hard tissues, such as dental anatomy which has high contrast variations or while using an intraoral scan. Dental tissues, unlike most breast tissues, particularly in patients with significant dental work containing metal, contain regions of extreme contrast variation. This contrast variation results in large truncation artifacts in reconstructed data which manifest in a reprojected radiograph. Truncation artifacts appear as multiple fine parallel lines immediately adjacent to high-contrast interfaces or as dark shading adjacent to high attenuation regions. They occur as a result of variations in the number of projections contributing to different regions in the reconstructed data. In addition, unlike breast tomosynthesis, the system geometry in dental tomosynthesis is not accurately known and the patient does not remain effectively static during scanning. In order to enable clinical usage at a range of positions in the mouth, an x-ray source may be mounted on a flexible arm. This arm is placed and aligned manually, with the expectation of significant variation in source placement depending on the user. In addition, the arm flexes and vibrates during the scan owing to the translation of the x-ray source. Second, breast tomosynthesis is also typically conducted with significantly larger pixel sizes and with the breast tissue fixed in place using an adjustable paddle. As a result, patient motion creates much more significant artifacts for intraoral tomosynthesis than for breast tomosynthesis. As such, it is necessary to measure the system geometry and patient position accurately. The simplest method involves the use of marker particles visible in the projections that can be used to determine the system geometry. Unfortunately, the use of marker particles generates artifacts in the reprojected radiograph.

Therefore, it would be desirable to have a device which allows for the provision of a low noise intraoral radiograph with features comparable to a standard radiograph given a low-dose tomosynthesis scan.

SUMMARY

Existing limitations associated with the foregoing, as well as other limitations, can be overcome by methods for using an invalidity matrix, iterative reconstruction and reprojection to generate from a three-dimensional reconstructed volume a two-dimensional image with image artifacts removed wherein the 3D reconstructed volume is based on a plurality of projection images. Herein, the plurality of projection images are processed by the iterative reconstruction algorithm to handle image artifacts by using a smooth deweighting process, discussed hereinafter, driven by an invalidity matrix to remove the image artifacts. By choosing an appropriate reprojection surface, the 3D reconstructed volume can be reprojected to get a final two-dimensional image with image artifacts removed wherein the final two-dimensional image has a greater area than the area of the sensor or wherein the final two-dimensional image is a synthetic two-dimensional radiograph with noise comparable that of a standard (non-synthetic) radiograph, Systems, apparatuses, and computer programs that operate in accordance with the methods also overcome the existing limitations.

According to an example embodiment herein, a method for generating a two-dimensional image from a 3D reconstructed volume based on a plurality of projection images comprises acquiring projections through an object to create projected images, calibrating the acquired projected images, estimating a geometry of the tomosynthesis system, determining an invalidity matrix for each acquired projection image, removing contributions of marker particles to the acquired projection images, constructing a starting volume for reconstruction, performing an iteration process for iteratively updating the starting volume, and reprojecting a final reconstructed volume to obtain a final two-dimensional image.

In one example embodiment herein, the acquiring includes performing a tomosynthesis scan including taking a number of projections at various locations over a scan angle. In an embodiment herein, the number of projections is 41. In another embodiment herein the scan angle is from a starting angle of −20° to finishing angle of 20° and a central projection occurs at the 0° angle.

In another example embodiment herein, the calibration procedure includes converting gray level values of pixels of projection images of a calibration phantom into an estimation of material thickness of the phantom. This can be utilized in an estimation of the material thickness of the object/dental anatomy.

In a further example embodiment herein, estimating the geometry of the tomosynthesis system includes using marker particles to determine the position of the dental anatomy in relation to the x-ray source.

In an example embodiment herein, determining an invalidity matrix includes identifying any invalid regions (e.g. projection edge, marker particles) in a binary mask and calculating the distance inside the invalid regions (positive) and the distance outside the invalid regions (negative) depending on whether the pixel in question is invalid. For example, starting with a binary definition of valid and invalid the distance of a pixel from its nearest valid pixel can be measured. This can, for example, be zero if the pixel itself is a valid pixel. The distance of that pixel from the nearest invalid pixel can also be measured. This can, for example, be zero if the pixel itself is invalid. These numbers may be combined to obtain a value for the pixel and the process repeated to obtain a value for each pixel of the selected projection, creating an invalidity matrix for said selected projection. The invalidity matrix enables the determination of the contribution to the reconstructed volume by each pixel in an acquired projection image during a volume update process of the iterative reconstruction.

In another example embodiment herein, removing contributions of marker particles to the acquired projection images includes subtracting portions of the image representing marker particles to create blank regions and interpolating the blank regions with fake data such as regions of the image close to the blank regions.

In yet another example embodiment herein, constructing a starting volume for reconstruction comprises constructing a starting volume for a first volume update process wherein said starting volume is a blank or empty volume.

In yet another example embodiment herein, performing an iteration process comprises iteratively updating a volume beginning with a starting volume in which the update is based on all acquired projections and the invalidity matrix for each projection such that image artifacts are removed. This process is further based on a smooth deweighting of pixels, driven by the invalidity matrix such that potentially problematic pixels contribute less to the volume to be updated than non-problematic pixels do. In yet another example embodiment herein, performing an iteration process further comprises testing against a termination criteria and repeating the iteration process if the termination criteria is not met.

In another example embodiment herein, reprojecting a final reconstructed volume includes determining a reprojection surface such that the field of view of a sensor if maximized. In yet another example embodiment herein, reprojecting a final reconstructed volume includes determining a reprojection surface such that a synthetic radiograph is obtained.

The method may be useful for increasing the effective size of a sensor to allow for viewing more teeth than can be seen with a standard sensor or for obtaining a standard size intraoral image on a patient who is unable to tolerate a sensor of standard size. The method may also be useful for obtaining a synthetic (non-standard) radiograph having a higher signal-to-noise ratio that that of any single projection image in a tomosynthesis scan. This can, for example, replace a standard, high dose, two-dimensional radiographic image taken separately by a dentist for analysis without the need to expose a patient to additional x-ray radiation after a tomosynthesis scan.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Different ones of the Figures may have at least some reference numerals that are the same in order to identify the same components, although a detailed description of each such component may not be provided below with respect to each Figure.

DETAILED DESCRIPTION

In accordance with example aspects described herein, methods, systems, apparatuses, and computer programs are provided for generating a two-dimensional image from a three-dimensional reconstructed volume based on a plurality of projection images.

X-Ray System

Figure 1:
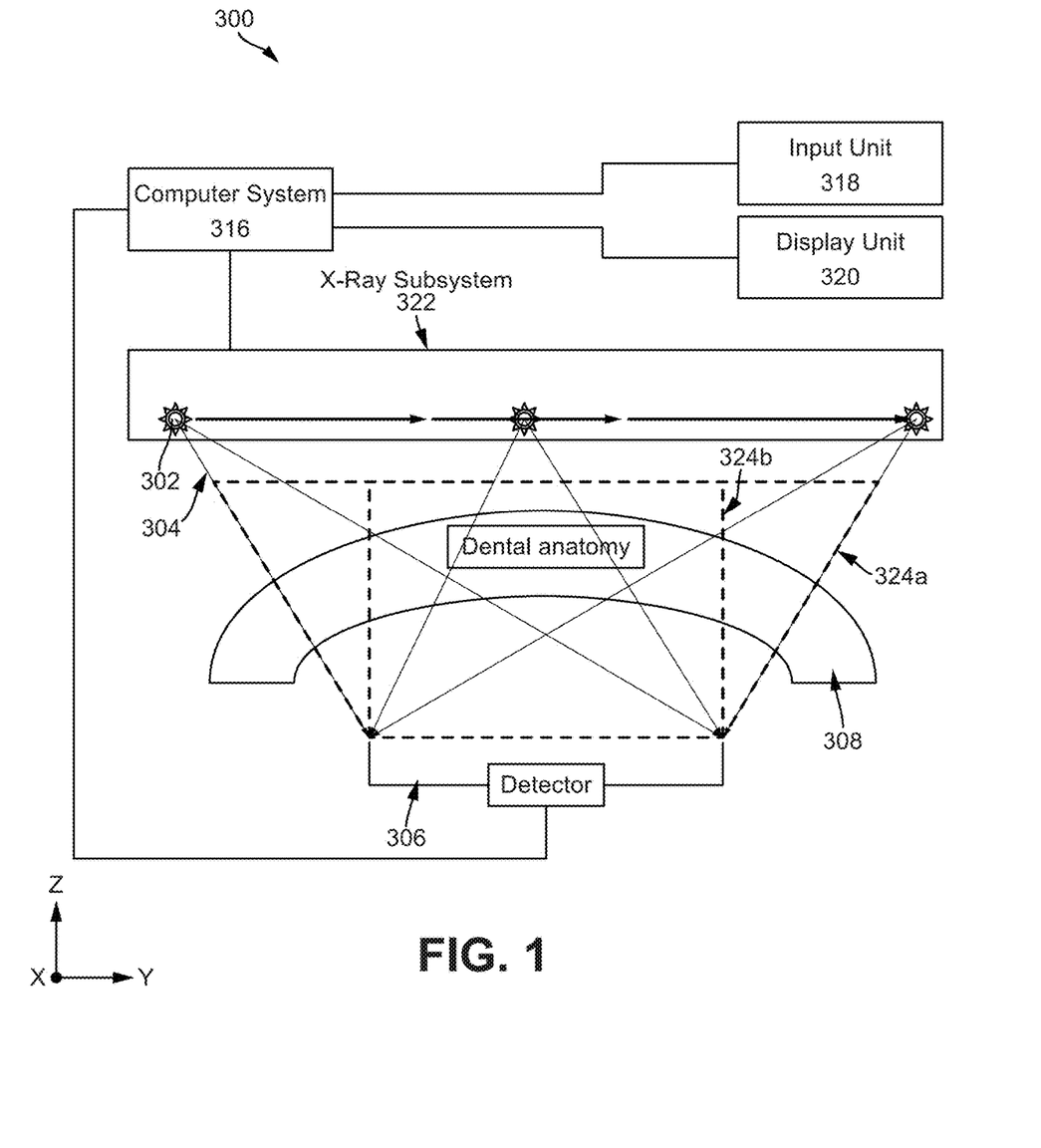
FIG. 1 illustrates a system illustrating how different portions of the anatomy are imaged by different projections.

FIG. 1 illustrates a block diagram of an intraoral x-ray system 300 for obtaining an intraoral images, and which is constructed and operated in accordance with at least one example embodiment herein. An x-ray detector 306 and an X-ray subsystem 322 are electrically connected to the computer system 316. The X-ray subsystem 322 comprises an X-ray source 302. The computer system 316 is electrically coupled to a user display unit 320 and a user input unit 318 with the user display unit 320 being an output and/or input user interface. As an x-ray source 302 moves from right to left, projections are taken and projection images of the dental anatomy 308 are formed on detector 306 for each projection, which images are collected by the computer system 316 for processing. The system 300 can be operated to obtain the one or more images of the dental anatomy 308 of interest, which may further include one or more sub-object (not shown). For example, the dental anatomy 300 may be a tooth (or teeth) and surrounding dentition of a patient, and the sub-object may be a root structure within the tooth.

The system 300 includes an x-ray detector 306 and an x-ray subsystem 322, both of which, including subcomponents thereof, are electrically coupled to the computer system 316. In one example embodiment herein, the x-ray subsystem 322 hangs from a ceiling or from a wall-mounted mechanical arm (not shown), so as to be freely positioned relative to the dental anatomy 308. The x-ray subsystem 322 further includes an x-ray source 302 which may be mounted on a motorized stage (not shown).

The x-ray detector 306 is positioned on one side of the object 50 and the receiving surface of the x-ray detector 306 extends in an x-y plane in a Cartesian coordinate system. The x-ray detector 306 can be a small intraoral x-ray sensor that includes, for example, a complementary metal-oxide semiconductor (CMOS) digital detector array of pixels, a charge-coupled device (CCD) digital detector array of pixels, or the like. In an example embodiment herein, the size of the x-ray detector 306 varies according to the type of patient as well as the volume of space in the buccal cavity available to be occupied by the x-ray detector. In an embodiment, small x-ray detectors 306 may be used by the system to obtain images with larger size than the size of the x-ray detector 306 by employing the processes discussed hereinafter. The x-ray detector 306 may also be one of a standard size employed in the dental industry. Examples of the standard dental sizes include a "Size-2" detector, which is approximately 27×37 mm in size and is typically used on adult patients, a "Size-1" detector, which is approximately 21×31 mm in size and is typically used on patients that are smaller than Size-2 adult patients, and a "Size-0" detector, which is approximately 20×26 mm in size and is typically used on pediatric patients. In a further example embodiment herein, each pixel of the x-ray detector 306 has a pixel width of 15 µm, and correspondingly, the Size-2 detector has approximately 4 million pixels in a 1700×2400 pixel array, the Size-1 detector has approximately 2.7 million pixels in a 1300×2000 pixel array, and the Size-0 detector has approximately 1.9 million pixels in a 1200×1600 pixel array. The color resolution of the x-ray detector 306 may be, in one example embodiment herein, a 12-bit grayscale resolution. Other examples include an 8-bit grayscale resolution, a 14-bit grayscale resolution, and a 16-bit grayscale resolution.

The x-ray source 302 is positioned on an opposite side of the dental anatomy from the x-ray detector 306. The x-ray source 302 emits x-rays 10 which pass through the dental anatomy 308 and are detected by the x-ray detector 306. The x-ray source 302 is oriented so as to emit x-rays 304 towards the receiving surface of the x-ray detector 306 in at least a z-axis direction of the Cartesian coordinate system as shown in FIG. 1, where the z-axis is orthogonal to the x-y plane associated with the receiving surface of the x-ray detector 306.

Figure 4:
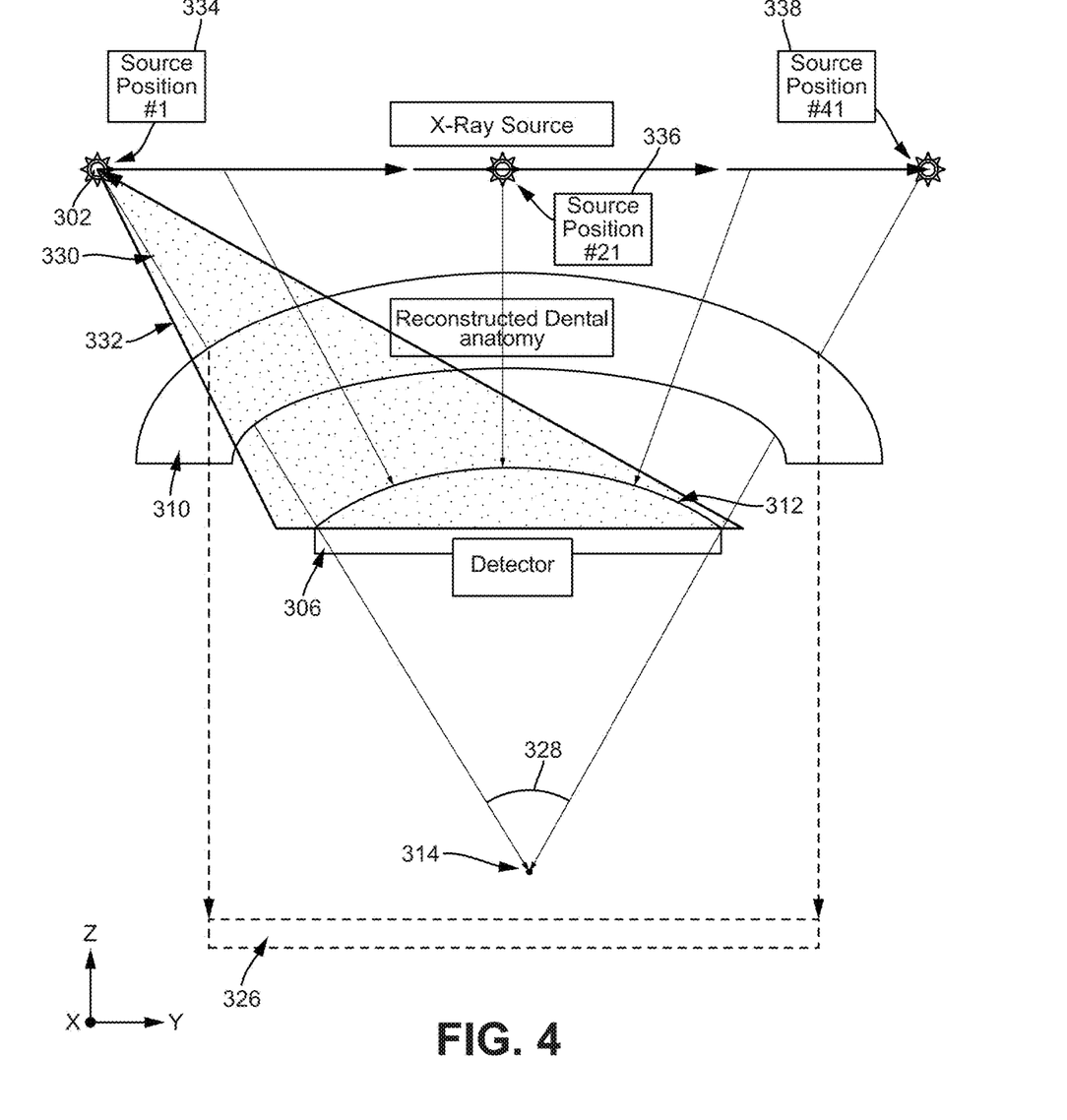
FIG. 4 shows a representation of how a reconstructed anatomy is reprojected onto a reprojection surface.

In one embodiment as shown in FIG. 1, the x-ray system is a tomosynthesis x-ray system wherein the x-ray source 302 can project x-rays 304 while positioned at each of multiple different locations within a scan angle 328 (shown in FIG. 4) where a 0° position in the scan angle 328 corresponds to the position for emitting x-rays 304 along the z-axis. In one example embodiment herein, the user initially positions the x-ray source 302, to a predetermined starting position relative to the dental anatomy 308. The computer system 316 then controls an on-board motor controller (not shown) to move the x-ray source 302 via a motorized stage (not shown), based on the known starting position, to step through each of the different locations within the scan angle 328. The computer system 316 can control the x-ray source 302 to cause the source 302 to emit x-rays 304 to project x-rays at each of those locations. In an example embodiment herein, there are 41 projections in the tomosynthesis scan and the scan angle ranges from −20° to +20° wherein the 0° position is the position of the x-ray source 302 at which x-rays are projected in the z-axis direction towards the x-ray detector 306 as shown in FIG. 4 (source position #21), and wherein source position #21 is the central source position 336, and wherein source position #41 is the last source position 338 in an example tomosynthesis system with 41 projections. The x-rays 304 may converge substantially at a focal spot 314. The focal spot 314 may however be located such that part of the x-rays projected from the outer limits of the scan angle 328, the outer limits corresponding to, for example, source position #1 and source position #41 miss the x-ray detector 306. The steps discussed hereinafter ensure, among other things, that contributions to a reconstructed volume by such x-rays that miss the detector (and thus detector pixels close to the edge of the detector 306) and by x-rays that hit marker particles (and thus pixels corresponding to marker particles in the projected image) are minimized.

In one example embodiment, the x-ray detector 306 may be an indirect type of detector (e.g., a scintillator x-ray detector) that first converts x-rays 304 into an optical image and then converts the optical image into the electrical signals, and in another example embodiment, the x-ray detector 306 may be a direct type of detector (e.g., a semiconductor x-ray detector) that converts x-rays 304 directly into the electrical signals. The computer system 316 processes the electrical signals to form a two-dimensional projection images which are processed to a reconstructed volume 310 and then to a final two-dimensional image of the dental anatomy. In one example embodiment herein, the image size of the two-dimensional projection image corresponds to the dimensions and the number of pixels of the x-ray detector 306. However the image size of the final two-dimensional image may be larger than the image size (the dimensions and the number of pixels) of the projection image and/or x-ray detector.

The system 300 may collect a plurality of projection images, as described above, by first positioning the x-ray source 302 at different angles, including at least the 0° position, and emitting x-rays 304 at each of those different angles through the dental anatomy 308 towards the x-ray detector 306.

Computer System for X-Ray Imaging

Having described a system 300 for generating a two-dimensional image from a three-dimensional reconstructed volume based on a plurality of projection images, reference will now be made to FIG. 2, which shows a block diagram of a computer system 600 that may be employed in accordance with at least some of the example embodiments herein. Although various embodiments are described herein in terms of this exemplary computer system 600, after reading this description, it will become apparent to a person skilled in the relevant art(s) how to implement the disclosure using other computer systems and/or architectures.

In one example embodiment herein, at least some components of the computer system 600 (such as all those components, or all besides component 628) can form or be included in the computer system 316 of FIG. 1. The computer system 600 includes at least one computer processor 622. The computer processor 622 may include, for example, a central processing unit, a multiple processing unit, an application-specific integrated circuit ("ASIC"), a field programmable gate array ("FPGA"), or the like. The processor 622 is connected to a communication infrastructure 624 (e.g., a communications bus, a cross-over bar device, or a network).

The computer system 600 also includes a display interface (or other output interface) 626 that forwards video graphics, text, and other data from the communication infrastructure 624 (or from a frame buffer (not shown)) for display on a display unit 628 (which, in one example embodiment, can form or be included in the display unit 320 of FIG. 1). For example, the display interface 626 can include a video card with a graphics processing unit.

The computer system 600 also includes an input unit 630 that can be used by a user of the computer system 600 to send information to the computer processor 622. In one example embodiment herein, the input unit 630 can form or be included in the input unit 318 of FIG. 1. The input unit 630 may include a keyboard device and/or a mouse device or other input device. In one example, the display unit 628, the input unit 630, and the computer processor 622 may collectively form a user interface.

In yet another embodiment that may include a touch screen, the input unit 630 and the display unit 628 may be combined, or may represent a same user interface. In such an embodiment, a user touching the display unit 628 can cause corresponding signals to be sent from the display unit 628 to the display interface 626, which can forward those signals to a processor such as processor 622. In an example embodiment herein, a system with a wall-mounted mechanical arm (not shown) may have a module attached to a wall wherein the module includes a processor 622 and on board electronics for controlling the x-ray source 304, a motorized stage (not shown) and communicating with the x-ray detector 306. Processor 622 can be configured to perform part (or all) of any of the procedures described herein. For example, one or more steps of the procedure illustrated in FIG. 3 can be stored on a non-transitory storage device in the form of computer-readable program instructions. To execute a procedure, the processor 622 loads the appropriate instructions, as stored on storage device, into memory 632, and then executes the loaded instructions.

Moreover, the computer system 600 may comprise a main memory 632, which may be a random access memory ("RAM"), and also may include a secondary memory 634. The secondary memory 634 may include, for example, a hard disk drive 636 and/or a removable-storage drive 638 (e.g., a floppy disk drive, a magnetic tape drive, an optical disk drive, a flash memory drive, and the like). The removable-storage drive 638 reads from and/or writes to a removable storage unit 640 in a well-known manner. The removable storage unit 640 may be, for example, a floppy disk, a magnetic tape, an optical disk, a flash memory device, and the like, which is written to and read from by the removable-storage drive 638. The removable storage unit 640 may include a non-transitory computer-readable storage medium storing computer-executable software instructions and/or data.

In further alternative embodiments, the secondary memory 634 may include other computer-readable media storing computer-executable programs or other instructions to be loaded into the computer system 600. Such devices may include a removable storage unit 644 and an interface 642 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 644 and interfaces 642 that allow software and data to be transferred from the removable storage unit 644 to other parts of the computer system 600.

The computer system 600 also may include a communications interface 646 that enables software and data to be transferred between the computer system 600 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCM-CIA") interface, and the like. Software and data transferred via the communications interface 646 may be in the form of signals, which may be electronic, electromagnetic, optical or another type of signal that is capable of being transmitted and/or received by the communications interface 646. Signals are provided to the communications interface 646 via a communications path 648 (e.g., a channel). The communications path 648 carries signals and may be implemented using wire or cable, fiber optics, a telephone line, a cellular link, a radio-frequency ("RF") link, or the like. The communications interface 646 may be used to transfer software or data or other information between the computer system 600 and a remote server or cloud-based storage (not shown).

One or more computer programs or computer control logic may be stored in the main memory 632 and/or the secondary memory 634. The computer programs may also be received via the communications interface 646. The computer programs include computer-executable instructions which, when executed by the computer processor 622, cause the computer system 600 to perform the processes as described herein and shown in FIGS. 3-9. Accordingly, the computer programs may control the computer system 316 and other components (e.g., the x-ray detector 306 and the x-ray source 302) of the intraoral tomosynthesis system.

In another embodiment, the software may be stored in a non-transitory computer-readable storage medium and loaded into the main memory 632 and/or the secondary memory 634 of the computer system 600 using the removable-storage drive 638, the hard disk drive 636, and/or the communications interface 646. Control logic (software), when executed by the processor 622, causes the computer system 600, and more generally the intraoral tomosynthesis system, to perform the processes described herein.

Lastly, in another example embodiment hardware components such as ASICs, FPGAs, and the like, may be used to carry out the functionality described herein. Implementation of such a hardware arrangement so as to perform the functions described herein will be apparent to persons skilled in the relevant art(s) in view of this description.

Method for Generating a Two-Dimensional Image from a Three-Dimensional Reconstructed Volume Based on a Plurality of Projection Images.

Figure 2:
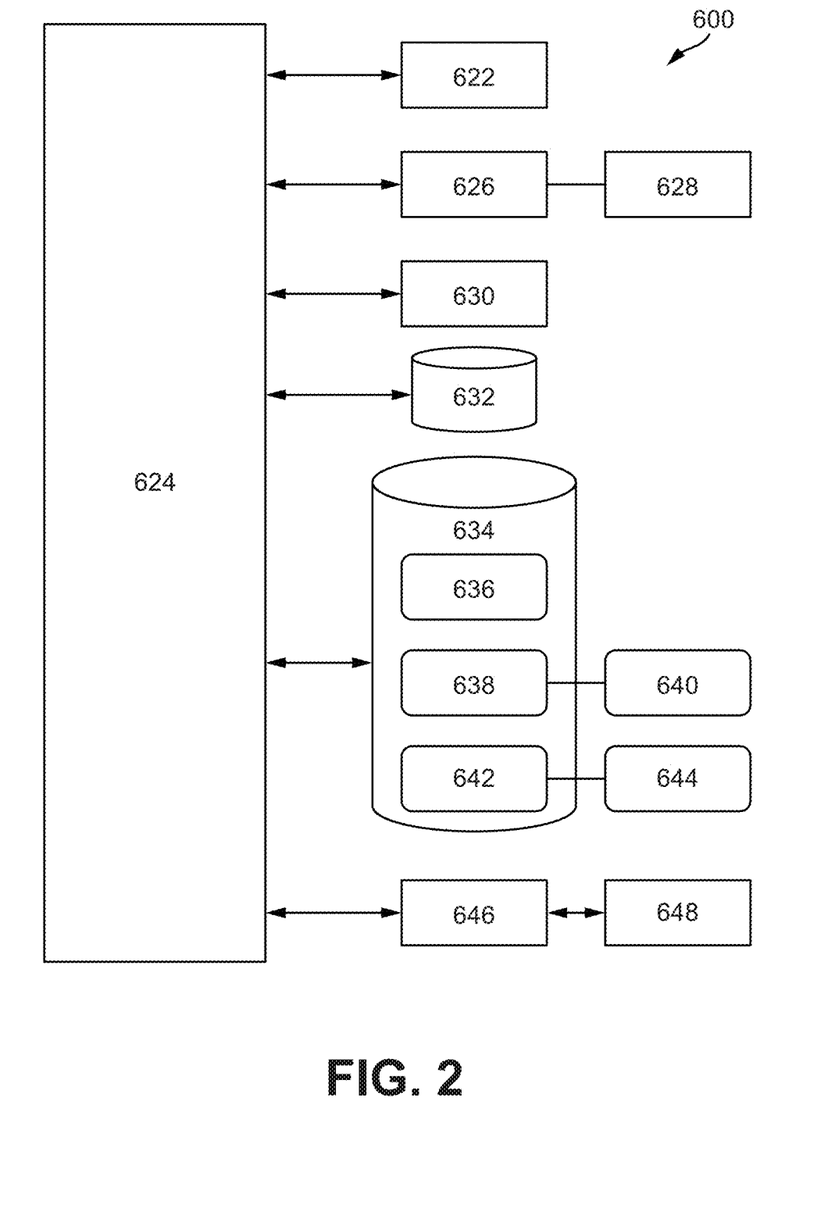
FIG. 2 illustrates a block diagram of an example computer system of the tomosynthesis system of FIG. 1.
Figure 3:
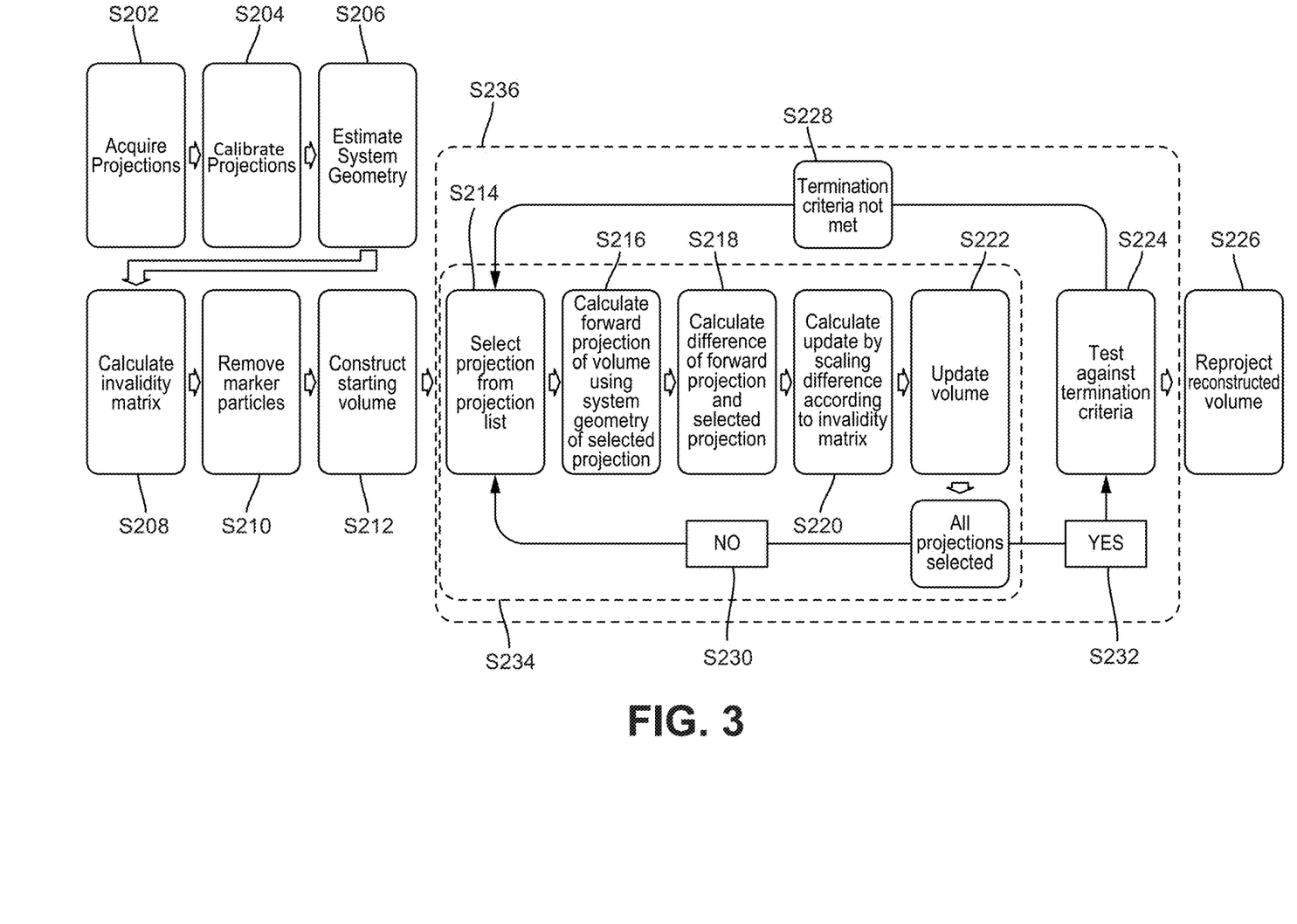
FIG. 3 is a flowchart illustrating the overall operation of a system using iterative reconstruction.

Having described the computer system 316 of FIG. 2, the intraoral tomosynthesis x-ray system 300 will now be further described in conjunction with FIG. 3, which shows a flow diagram of a process according to an example embodiment herein for using an invalidity matrix, a reconstruction process and a reprojection process to generate a two-dimensional image from a three-dimensional reconstructed volume based on a plurality of projection images In Step S202 the intraoral tomosynthesis system 300 acquires a plurality of projection image of the dental anatomy 308 for different spatial position of the x-ray source during a tomosynthesis scan. For example, the x-ray source 302 is moved by a motorized stage (not shown) and control circuitry to different positions within the scan angle 328, and the computer system 316 controls the x-ray source 302 to emit x-rays 304 at each position. In one example embodiment herein, x-ray source 302 is scanned, by moving the x-ray source from −20° at source position #1, 334 where a first projection 330 is made to obtain a first projection image, through 0° at source position #21, 336 where a central projection is made to obtain a central projection image, to −20° at source position #41, 338 where a final projection is made to obtain a final projection image. In an embodiment herein 41 projections are made in a single tomosynthesis scan in evenly distributed increments of 1° to provide 41 scan angles, including one at the 0° position, although this example is not limiting. It can be seen that in some projections, for example in the first projection 330, not all individual x-rays 332 of that first projection hit the detector 306.

X-rays 304 that pass through the dental anatomy 308 are attenuated by the dental anatomy 308 before being projected onto the x-ray detector 306. The x-ray detector 306 converts the x-rays 110 into electrical signals and provides the electrical signals to the computer system 316. The computer system 316 processes the electrical signals collected at each scan angle position to acquire the plurality of projection images, each image comprising an array of pixels. The image acquired with the x-ray source 302 at the 0° position is also referred to herein as a central projection image. The computer system 316 then performs in Step S204 a calibration of the acquired projection images by converting gray level values of the projection images into material thickness based on an earlier projection using a phantom calibration object of known dimensions.

In Step S206, an associated system geometry is estimated by using marker particles in the tomosynthesis scan to determine the position of the dental anatomy in relation to the X-ray source. An invalidity matrix, discussed hereinafter, may then be determined in Step S208 for each acquired projection image to determine the contribution of pixels the acquired image to a reconstructed volume during an update Step S222 of the iterations S236 discussed hereinafter. Contribution of marker particles to the projection images can be identified and removed in Step S210 such that their further contribution to a volume to be reconstructed 310 is limited. Removal of said marker particle contributions from the projection images can be achieved by identifying regions in the projection images that correspond to the shape of the marker particles and subtracting them from the projection images. The resulting blank regions of the projection images can then padded by, for example, interpolating said blank regions with data of the surrounding regions. However the padded data is essentially fake data and this information can be further propagated to the volume to be reconstructed 310. A smooth deweighting process based on an invalidity matrix of all pixels, discussed hereinafter, helps to limit this further contribution. Herein pixels corresponding to the fake padded data as well as pixels close to the edges of the detector (collectively referred to as potentially problematic pixels) can be weighted for each projection image such that they do not contribute to the volume to be reconstructed 310 as much as other pixels do.

A starting volume 324a, depicted in FIG. 1 for a first volume update process wherein said starting volume 324a is a blank or empty volume can be constructed in Step S212 and a projection selected in Step S214 from a projection list for calculating a forward projection of the starting volume in Step S216 using the system geometry of the selected projection. This starting volume will be iteratively updated in the volume update steps S234 and iteration steps S236 discussed hereinafter to reconstruct the irradiated dental anatomy.

In an example embodiment, the number of projections may be 41 and a number of iterations S236 may be 5 or 6. Therefore 41 volume update steps S234 are executed in each iteration step S236 for said example embodiment.

In another embodiment herein, a first volume update step S234 for reconstructing the irradiated dental anatomy can be started in a first iteration S236 using a first selected projection image wherein the volume update step S234 is subsequently repeated for the remaining projection images during said first iteration S236. Stored projections images may be selected in succession such that a selected projection image is from a projection position that located away from the projection position of the previously selected projection image such that the two projection images are substantially different from each other. For example, every nth projection image can be selected successively wherein n does not divide the total number of projection images evenly. In an exemplary embodiment, n can be 7. Alternatively projection images of projection positions that are furthest apart from each other in the scan angle 328 may be selected successively.

Figure 9:
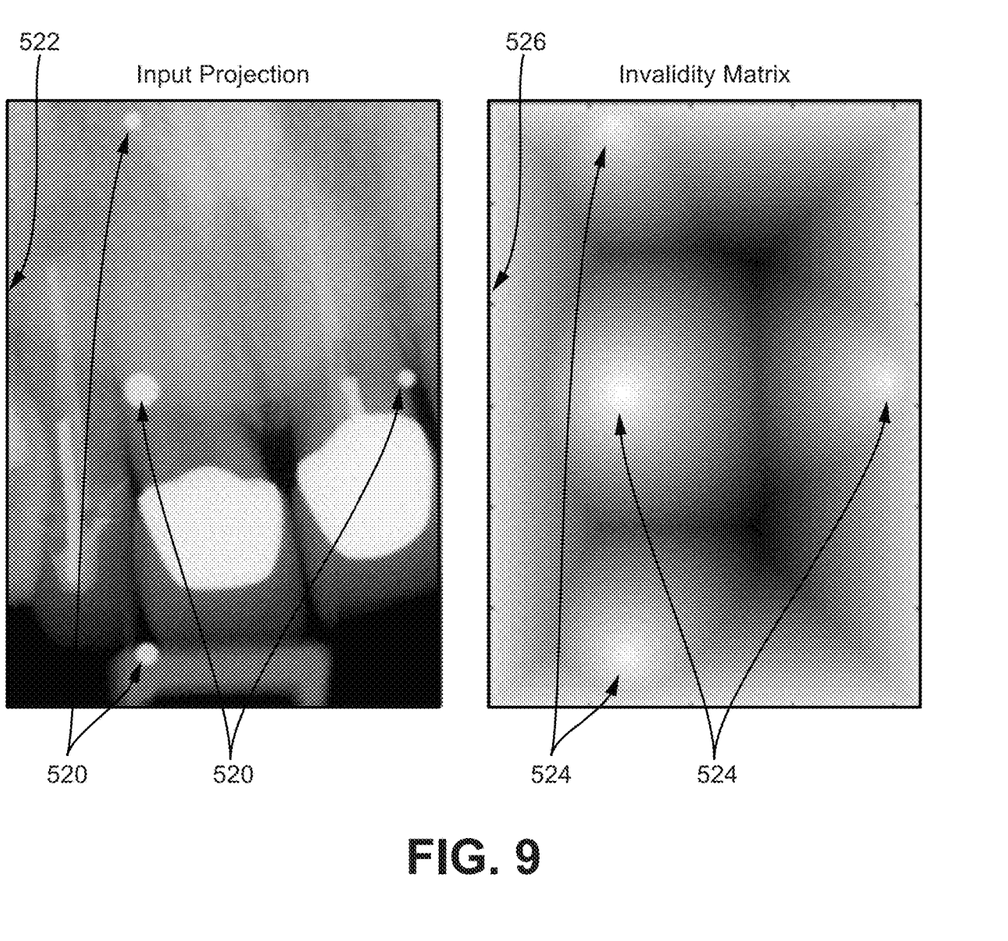
FIG. 9 illustrates a grayscale representation of the invalidity matrix and the corresponding selected input projection.

In the first volume update Step S234, a first projection image is selected in Step S214. A forward projection of the starting volume is then determined in Step S216 using the system geometry. A difference image between the resultant forward projection and the selected projection, which contains the padded data, is determined in Step S218. An update for updating the starting volume is calculated in Step S220 by scaling said difference image according to the invalidity matrix for the projection. The invalidity matrix is a matrix that ensures that the contribution, of potentially problematic pixels (pixels close to the edge of the detector and pixels representing padded data) to the update of the reconstructed volume (or starting volume in the case of a first volume update S234 of a first iteration S236) is limited. The invalidity matrix for all projection images can be calculated in Step S208 by identifying any invalid regions (potentially problematic pixels) in a binary mask and calculating the distance inside the invalid regions (positive) and the distance outside the invalid regions (negative) depending on whether the pixel in question itself is valid or invalid. For example, staring with a binary definition of valid and invalid the distance of a pixel from its nearest valid pixel can be measured. This can, for example, be zero if the pixel itself is a valid pixel. The distance of that pixel from the nearest invalid pixel can also be measured. This can, for example, be zero if the pixel itself is invalid. These numbers may be combined to obtain a value for each pixel of a projection image and the process repeated to obtain a value for each pixel of the selected projection, creating an invalidity matrix for said selected projection image as shown in FIG. 9 wherein potentially problematic pixels of the projection image include portions of the image representing marker particles 520 and edges of the image 522. In the adjacent image, a representation of the invalidity matrix is shown. Values corresponding to pixels closest to the potentially problematic pixels are shown to have a lighter color (or shorter distance) than values corresponding to pixels furthest from the potentially problematic pixels which have a darker color (or larger distance). It can be seen that portions of the invalidity matrix 524, 526 corresponding to the potentially problematic pixels will have the shortest distances since they coincide with the potentially problematic pixels. Therefore pixels with shorter distances will contribute less to the reconstructed volume than pixels with larger distances will. After scaling the difference image according to the invalidity matrix to obtain an update, the starting volume (blank or empty volume) is updated by backprojecting the difference image through said starting volume to obtain a first reconstructed volume in Step S222. The first reconstructed volume is then processed further volume update processes S234 using subsequent selected projection images until all projection images have been selected. If a termination criteria, discussed hereinafter, is not met the iteration steps S236 are repeated.

The update of the volume in Step S222 may comprise a Simultaneous Algebraic Reconstruction Technique (SART) based iterative reconstruction algorithm wherein the volume V is updated by summing the currently estimated volume with a backprojected volume according to the formula $V \rightarrow V + \Delta W V_i(BP_i(EP_i))$.

This may take inputs:

$P_i$, where i denotes the ith measured/selected projection P in Step S214 and P is a two-dimensional matrix corresponding to the projected image.

BP$_i$, where i denotes the ith backprojection operator which is used to alter the voxels in a reconstructed volume to make them consistent with the measured projections FP$_i$, where i denotes the ith forward projection operator obtained in Step S216, wherein the forward projection operator is an operator used to calculate the projection resulting from a volume with specific volume content Δ, which is a scaling factor used to control convergence speed, described hereinafter.

WV$_i$, which is a volumetric weighting matrix, described hereinafter and

V, which is the currently estimated volume.

This may be accomplished by the following steps:

1. Start with an uninitialized volume V as shown in Step S212.
2. Compute an error/difference image EP$_i$=FP$_i$(V)–P$_i$, as shown in Step S218.
3. Update the volume V according to: V→V+ΔWV$_i$(BP$_i$(EP$_i$)), for each i as in Step S222. The ordering of the update in terms of i can be non-consecutive because it speeds convergence.

In an example embodiment herein, each iteration of an update process can be thought of as multiplying an error term associated with the iteration by a number. If that number has a magnitude less than one, each iteration will reduce the error term and the process converges. If the number is greater than one, the error term increases and the process diverges. As such, the convergence factor is chosen to be as high as possible without exceeding a certain threshold value since fewer iterations are better. Beyond the threshold, the iterations diverge and each iteration becomes increasingly far from the desired volume.

In an example embodiment herein, a goal of the volume update may be to construct a final volume such that the difference image EP$_i$ is close to zero.

Each pixel of a projection image can be represented by a three-dimensional equivalent known as a voxel. WV$_i$ represents an "ith" volumetric weighting matrix which determines how much weight should be given to each voxel of the back projection "ith" error image when determining said voxel's contribution to the volume that is about to be updated during a volume update process S234. This allows the removal of the contributions of invalid pixels of the "ith" projection from the reconstructed volume.

WV$_i$, may be obtained as follows:

An invalidity I$_i$ is obtained according to the ternary/conditional notation below such that $$I_i = BP_i(IP_i) < -d \; ? \; 0 : \frac{(BP_i(IP_i + d))}{r}$$

wherein d is a term indicating a distance from invalid regions where a voxel is considered completely valid and r is a scaling factor chosen to provide a scale based on the extent of perturbations to data based on edge effects related to marker identification.

The ith invalidity matrix IP$_i$ may be computed as:

IP$_i$=DI$_i$>DO$_i$?DI$_i$:−DO$_i$, wherein

IP$_i$ is the ith invalidity matrix and P$_i$ is a two-dimensional matrix corresponding to the projected image.

DI$_i$ is the distance from the nearest valid pixel for a given pixel

DO$_i$ is the distance from the nearest invalid pixel for a given pixel.

The invalidity I$_i$ may then be used to calculate the weighting term for update:

$$WV_i = \frac{1}{(1 + I_i)^2}$$

The above steps can be used to iteratively reconstruct the volume using the invalidity matrix. A grayscale representation of the invalidity matrix and the corresponding selected input projection is shown in FIG. 9. Since the invalidity matrix reduces the contribution of invalid pixels to the reconstructed volume, the reconstructed volume may contain little to no influence by marker particles. After a first update of the reconstruction volume, a next non-consecutive projection image can be selected such that it is different from the first projection and the process may be repeated S230 with the newly reconstructed volume being used for a new forward projection in Step S216. It can be goal to obtain a reduction in the difference image with each newly selected projection until the difference image is close to zero. The volume update process S234 is repeated until all projections are selected. After all projections are selected S232, a second iteration S236 involving all projections may be started if a termination criteria is not met. By testing against said termination criteria in Step S224, a new iteration S236 may be started if the termination criteria is not met S228 with the current reconstructed volume being used for the forward projection. Alternatively the reconstruction may be ended if the termination criteria is met. The termination criteria can be for example (i) the difference of forward projection and selected projection or a function of said difference of forward projection and selected projection being close to zero or (ii) a fixed number of iterations steps S236 having been completed. The fixed number can, for example, be between 5 and 10. Upon meeting the termination criteria, a reprojection surface may be calculated and the final reconstructed volume may be reprojected in Step S226 to obtain a 2D Image with an extended field of view. The extended field of view is obtained as follows. Each pixel of the reprojection surface can have properties such as an x-position, a depth position and a direction which may be determined by the direction between the pixel of the reprojection surface and the position of a virtual focus 314. Starting at an extreme end of the reconstructed volume 310, voxels intersected by a line determined by the pixel position and direction may be summed to determine the total attenuation of the pixel. This may be repeated for all pixels of the reprojection surface to obtain a 2D Image with an extended field of view. Thus, using the virtual focus 314 at negative depth (past the position of the detector 306 in the opposite direction of the x-ray source) that is matched to the opening angle of the scan angle 328 of the tomosynthesis scan, the reconstructed dental anatomy 310 may be projected onto the reprojection surface 312 to obtain an image that includes a larger area than that available for a single detector system with no extended field of view. The larger area is illustrated as the surface of the effective detector 326 in the x-y plane of FIG. 4. FIG. 4 also shows a representation of how the reconstructed volume 310 is reprojected onto the reprojection surface 312 wherein the reprojection surface 312 is for example a semi-circular surface containing pixels. The reprojection surface can also be dynamically constructed to match the geometry of the dental anatomy. A dynamically obtained surface that matches the geometry of the dental anatomy can be based on the reconstructed volume 310.

Figure 5:
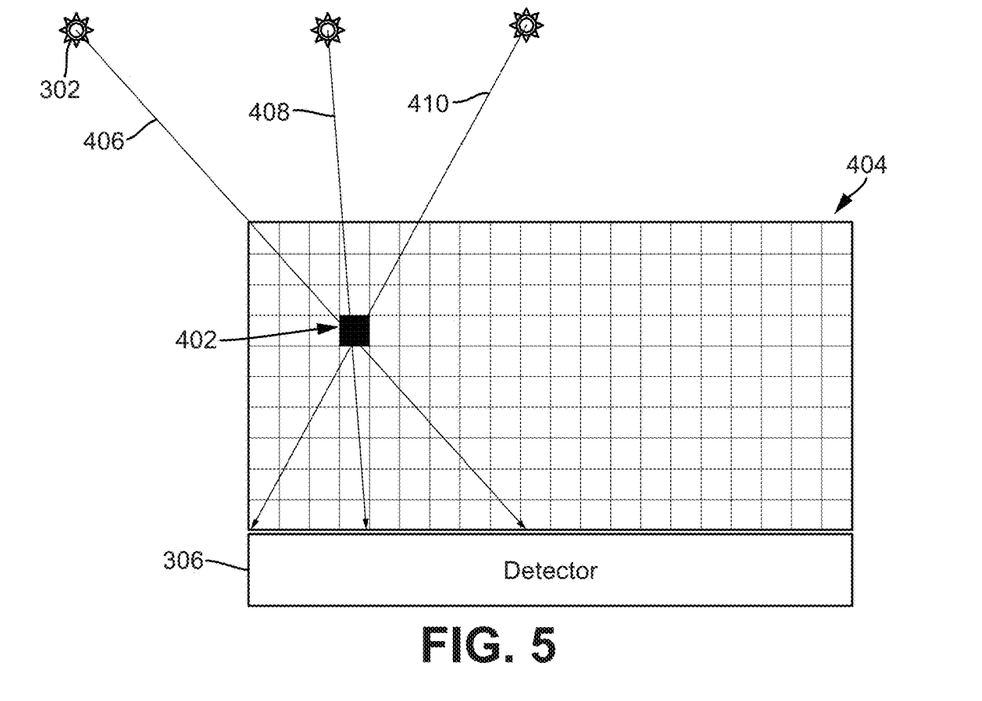
FIG. 5 illustrates how discontinuities from variation of support are generated in non-iterative reconstructions.
Figure 6:
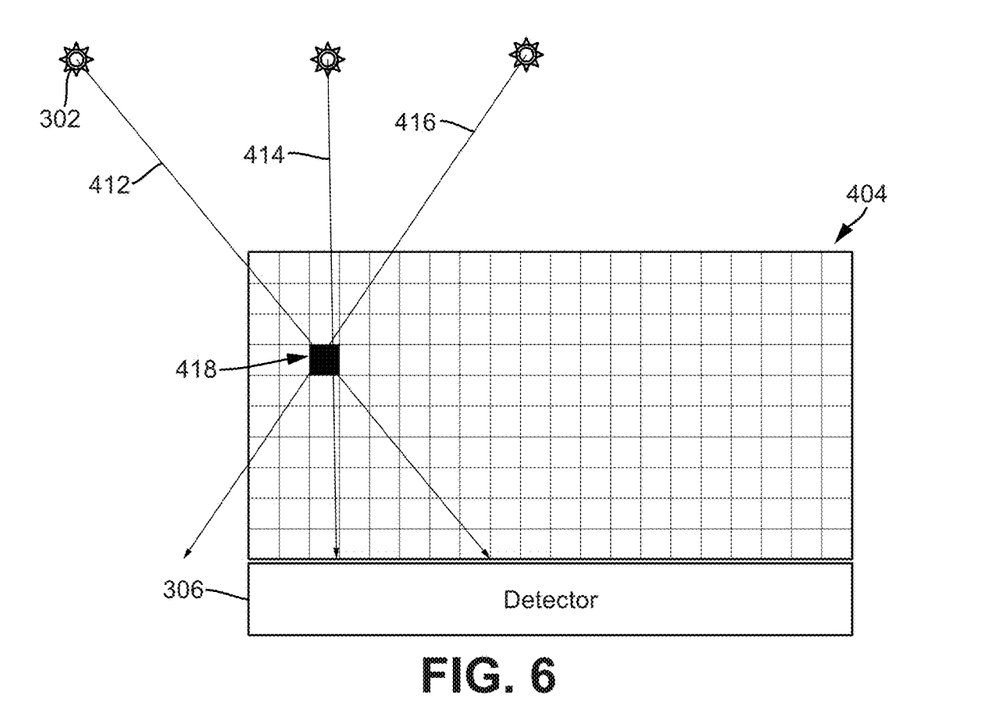
FIG. 6 illustrates how discontinuities from variation of support are generated in non-iterative reconstructions.

FIGS. 5 and 6 illustrate how discontinuities from variations in support are generated in non-iterative reconstructions, support being a representation of the number of projections that contribute to a given voxel. Voxels 402 and 418 are adjacent voxels In FIG. 5, rays 406, 408 and 410 of three different projections pass through voxel 402 of volume 404 and result in all projections contributing to voxel 402. In FIG. 6, rays 412, 414 and 416 of three different projections pass through voxel 418 of volume 404 but only projections corresponding to rays 414 and 412 contribute to voxel 418. The projection corresponding to ray 416 does not contribute to voxel 418 during reconstruction, because ray 416 is not incident on detector 306 and as such ray 416 does not contribute to the formation of any pixels of the projection image. Each pixel of the projection image has a three-dimensional equivalent known as a voxel. A difference in the number of projections contributing to adjacent voxels 402 and 418 in FIGS. 5 and 6 will generate discontinuity in the reconstructed volume.

Figure 7:
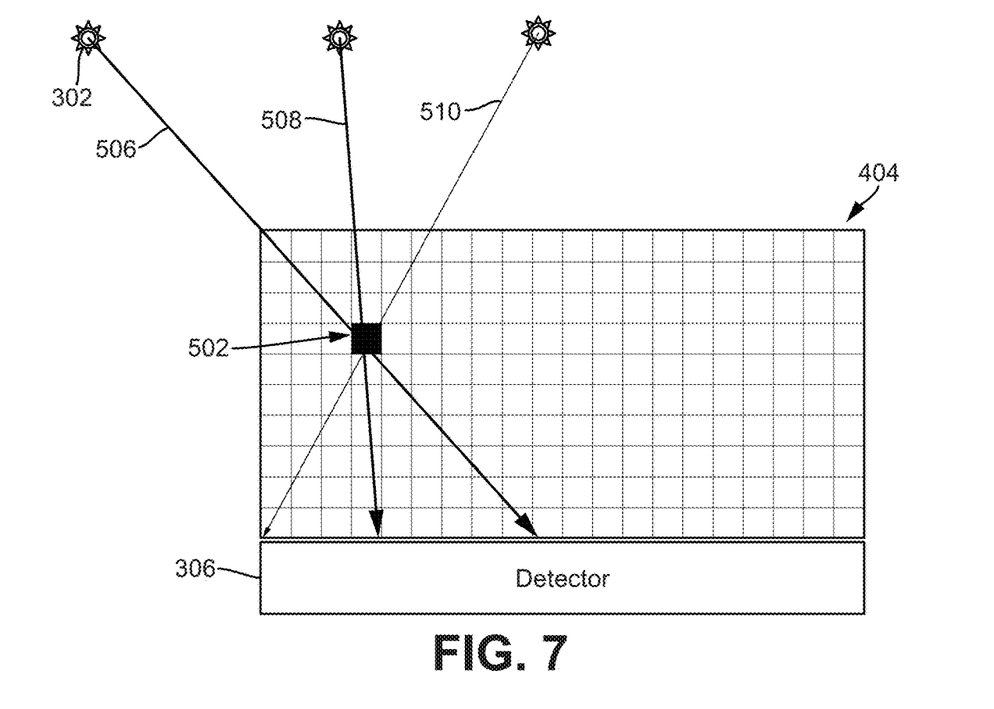
FIG. 7 illustrates the use of an invalidity matrix in an iterative reconstruction.
Figure 8:
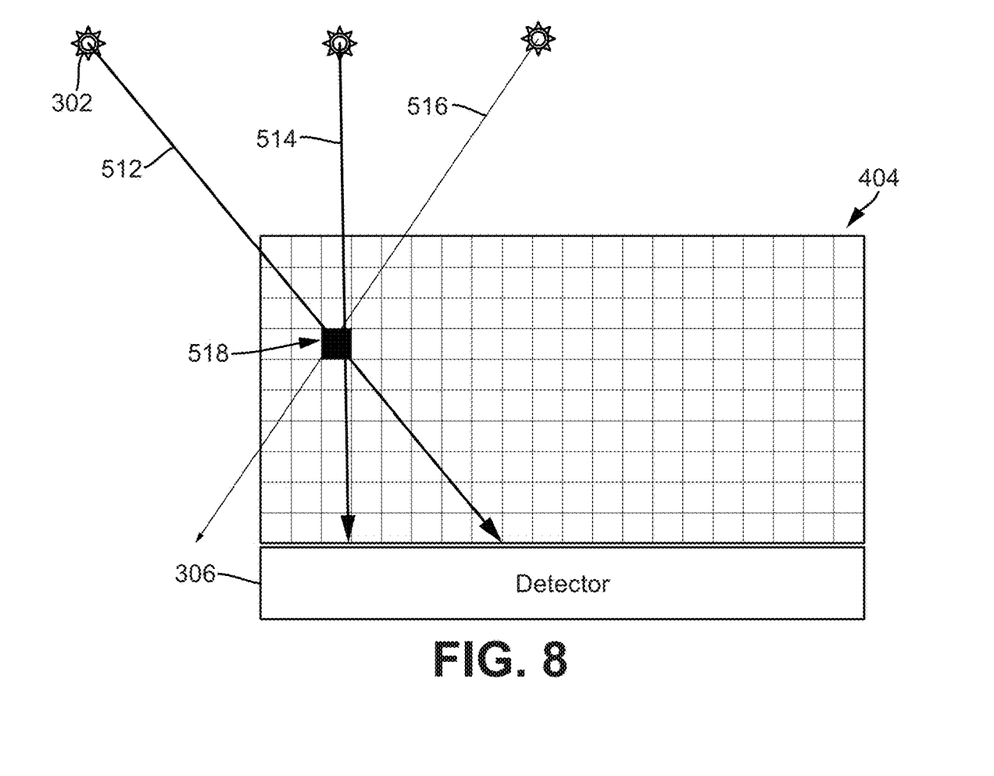
FIG. 8 illustrates the use of an invalidity matrix in an iterative reconstruction.

FIGS. 7 and 8 illustrate the use of an invalidity matrix in an iterative reconstruction to reduce or eliminate discontinuities in reconstructed volumes. Voxels 502 and 518 are adjacent voxels. In FIG. 7, three different projections corresponding to rays 506, 508 and 510 respectively all contribute to voxel 502 since the rays are all incident on the detector 306. Projections corresponding to rays 506 and 508 however contribute more to voxel 502 than the projection of ray 510 does. This is because contributions of pixels close to the detector edge are deweighted according to the invalidity matrix during an update step of the iterative reconstruction process since not all rays corresponding to projections that are incident close to the edges of the detector fall on the detector.

In FIG. 8, a projection of ray 516 misses contribution to voxel 518. Projections of rays 512 and 514 however contribute to voxel 518. A difference in the number of projections contributing to adjacent voxels does not generate discontinuity here because the contribution of near edge pixels to the reconstruction is near zero according to the invalidity matrix. As can be seen in FIG. 8, pixels of projections corresponding to rays 512 and 514 are weighted during an update step of the iterative reconstruction according to the invalidity matrix to contribute more to voxel 518 while the contribution of pixels of the projection of ray 516 is near zero. This results in a reconstructed three-dimensional volume 310 that is more representative of the irradiated dental anatomy 308 in preparation for the reprojection step of Step S226 discussed above.

Further, a synthetic radiograph having a higher signal-to-noise ratio that that of any single projection image in a tomosynthesis scan may be obtained by the above processes wherein the reconstruction done is smaller and a flat plane reprojection surface having the same size as the detector is selected for reprojection. For a smaller reconstruction, a smaller starting volume 324b may be chosen wherein said smaller starting volume 324b may be a blank or empty volume the length in the X-Y plane of which matches the length of the detector 306 in said X-Y plane as shown in FIG. 1. For starting volume 324b, fewer projections incident at the edges of the detector will be used in the iterative reconstruction process compared to the number of projections incident at the edges of the detector that are used when employing a bigger volume 324a. In consequence, artifacts in the reconstruction are reduced. Further a flat plane reprojection surface having the same length as the length of detector in the X-Y plane can be used for reprojection using the processes described above and shown in FIG. 3. Herein, a virtual focus at negative depth is not used. Rather x-rays are projected through the reconstructed volume programmatically by applying a forward projection operator of the central source position to the reconstructed volume to obtain a 2D image with the same field of view as that of the detector. This results in a 2D image which has much noise removed and thus possesses a much higher signal-to-noise ratio than that of any single projection image in the low dose tomosynthesis scan while showing more features of the scanned dental anatomy than a single center projection shows. This is helpful in a setting where both an intraoral radiograph and a dental tomosynthesis scan is needed to provide by a dentist. In an embodiment herein, such an image may be obtained primarily to allow the presentation of a 2D radiograph without marker particles using a 3D tomosynthesis scan and eliminating the need to take a separate high dose radiograph for use by a dentist.

Figure 10:
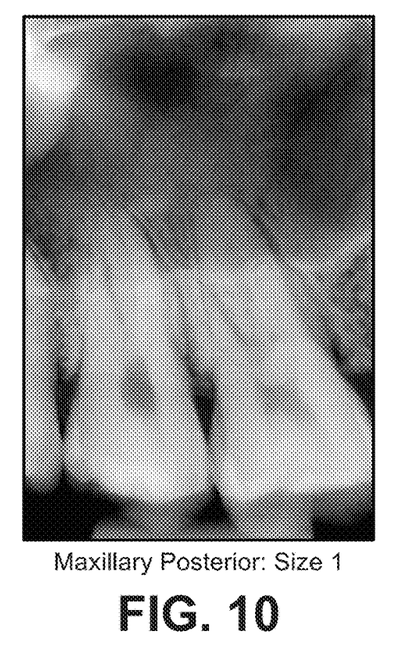
FIG. 10 illustrates an x-ray image of the maxillary anterior region of a patient taken with a size 1 sensor.
Figure 11:
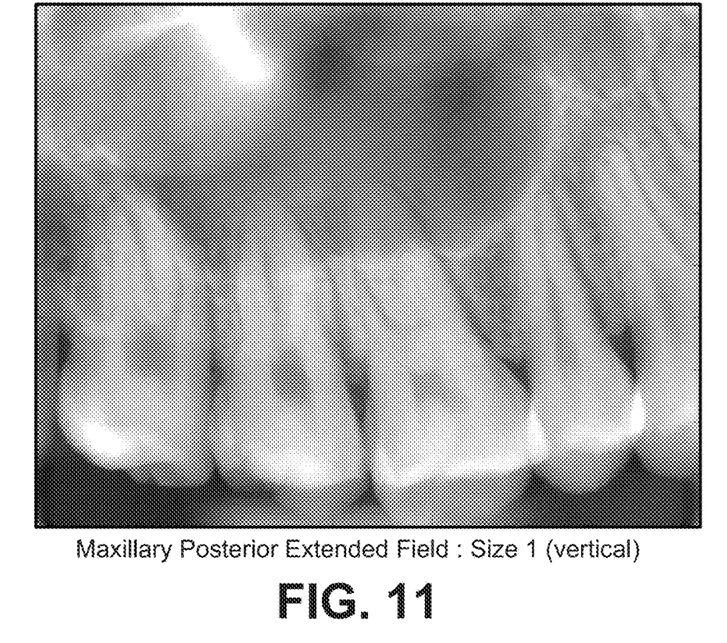
FIG. 11 illustrates an image of same maxillary anterior region of FIG. 10 with the image having an extended field of view according to an embodiment herein.

FIGS. 10 and 11 illustrate images of the maxillary anterior region of a patient taken with a size 1 sensor. In FIG. 10 a system without the extended field of view described herein is used to take a single high dose radiograph and results in an image having the same field of view as the sensor used. FIG. 11 shows that a larger field of view can be obtained at a low dose with a tomosynthesis x-ray system having the extended field of view described herein.

The general operation of the x-ray system according to the disclosure may be as follows. A dentist may, for example, note that a patient has a painful torus behind said patient's left molars. In addition, the patient may have extensive tooth decay that the dentist may like to image using an intraoral scan prior to assessing the need for a bridge. The dentist may therefore use a size 1 sensor oriented vertically to form an image using the system disclosed herein, said image being somewhat larger than the image of a size 2 sensor oriented horizontally using convention x-ray systems. Therefore a dentist may use a smaller, easier to fit, sensor to obtain an image with similar or larger size than that obtained from a larger sensor that doesn't fit in a given patient's mouth. Without this approach, the most expeditious approach would be to take several images while shifting the sensor manually and stitching them together by eye. This would invariably complicate the dentist's understanding of the problem since no single image may contain the entirety of the problem region. Moreover, if the primary goal of a dentist is to obtain a standard 2D radiograph with a high signal to noise ratio than that of any single projection image in a low dose tomosynthesis scan without taking an additional high dose radiograph, a device according to the disclosure wherein the reprojection surface is a flat plane may be similarly used to produce such a 2D image.

In view of the foregoing description, it can be appreciated that the example embodiments described herein provide systems, methods, apparatuses, and computer programs products for using an invalidity matrix, iterative reconstruction and reprojection to generate from a three-dimensional reconstructed volume a two-dimensional image with image artifacts removed wherein the 3D reconstructed volume is based on a plurality of projection images Unless otherwise defined, all technical and scientific terms used herein have the same meaning as commonly understood by one of ordinary skill in the art to which this invention belongs. Although methods and materials similar to or equivalent to those described herein can be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. A method for generating a two-dimensional image from a three-dimensional reconstructed volume based on a plurality of projection images, the method comprising:
   acquiring the plurality of projection images of a dental anatomy on a detector;
   determining an invalidity matrix for each projection image of the plurality of projection images;
   constructing a starting volume for reconstruction;
   performing an iteration process to iteratively update the starting volume to obtain a reconstructed volume; and
   reprojecting the reconstructed volume to obtain said two-dimensional image when a termination criteria is met,
   wherein the iteration process includes selecting a projection image of the plurality of projection images, and
   wherein the iteration process further includes a deweighting process driven by the invalidity matrix to remove the contributions of potentially problematic pixels of the selected image projection to the reconstructed volume.

2. The method according to claim 1, further comprising removing contributions of marker particles to the plurality of projection images.

3. The method according to claim 1, wherein the number of the plurality of projection images is 41.

4. The method according to claim 1, wherein the determining step further includes identifying any invalid regions in a binary mask, calculating the distances of each pixel from its nearest valid and invalid pixels and combining said distances to obtain a value for each pixel.

5. The method according to claim 1, wherein the starting volume is a blank volume.

6. The method according to claim 1, wherein the reprojecting step further includes using dimensions of a reprojection surface and size of the starting volume to control at least one characteristic of the two dimensional image.

7. The method according to claim 6, wherein the reprojection surface is a semi-circular surface.

8. The method according to claim 6, further comprising using a virtual focus at negative depth that is matched to an opening angle of a scan angle of a tomosynthesis scan to reproject the reconstructed dental anatomy onto the reprojection surface to obtain said two-dimensional image wherein said two-dimensional image has a larger field of view than the field of view of the detector.

9. The method according to claim 6, wherein the reprojection surface is dynamically constructed to match the geometry of the dental anatomy.

10. The method according to claim 6, wherein the reprojection surface is a flat plane.

11. A system for generating a two-dimensional image from a three-dimensional reconstructed volume based on a plurality of projection images, the system comprising:
    at least one processor operable to:
    acquire the plurality of projection images of a dental anatomy on a detector;
    determine an invalidity matrix for each projection image of the plurality of projection images;
    construct a starting volume for reconstruction;
    perform an iteration process to iteratively update the starting volume to obtain a reconstructed volume; and
    reproject the reconstructed volume to obtain said two-dimensional image when a termination criteria is met,
    wherein the iteration process includes selecting a projection image of the plurality of projection images, and
    wherein the iteration process further includes a deweighting process driven by the invalidity matrix to remove the contributions of potentially problematic pixels of the selected image projection to the reconstructed volume.

12. The system according to claim 11, wherein the processor is operable to remove contributions of marker particles to the plurality of projection images.

13. The system according to claim 11, wherein the number of the plurality of projection images is 41.

14. The system according to claim 11, wherein the processor is operable to determine the invalidity matrix by identifying any invalid regions in a binary mask, calculating the distances of each pixel from its nearest valid and invalid pixels and combining said distances to obtain a value for each pixel.

15. The system according to claim 11, wherein the starting volume is a blank volume.

16. The system according to claim 11, wherein the processor is operable to reproject by using dimensions of a reprojection surface and size of the starting volume to control at least one characteristic of the two dimensional image.

17. The system according to claim 16, wherein the reprojection surface is a semi-circular surface.

18. The system according to claim 16, wherein the processor is operable to use a virtual focus at negative depth that is matched to an opening angle of a scan angle of a tomosynthesis scan to reproject the reconstructed dental anatomy onto the reprojection surface to obtain said two-dimensional image wherein said two-dimensional image has a larger field of view than the field of view of the detector.

19. The system according to claim 16, wherein the reprojection surface is dynamically constructed to match the geometry of the dental anatomy.

20. The system according to claim 16, wherein the reprojection surface is a flat plane.

21. A non-transitory computer-readable storage medium storing a program which, when executed by a computer system, causes the computer system to perform a procedure comprising:
    acquiring a plurality of projection images of a dental anatomy on a detector;
    determining an invalidity matrix for each projection image of the plurality of projection images;
    constructing a starting volume for reconstruction;
    performing an iteration process to iteratively update the starting volume to obtain a reconstructed volume; and
    reprojecting the reconstructed volume to obtain said two-dimensional image when a termination criteria is met,
    wherein the iteration process includes selecting a projection image of the plurality of projection images, and
    wherein the iteration process further includes a deweighting process driven by the invalidity matrix to remove the contributions of potentially problematic pixels of the selected image projection to the reconstructed volume.

* * * * *